United States Patent [19]
Schaefer et al.

[11] Patent Number: 5,863,521
[45] Date of Patent: Jan. 26, 1999

[54] LIQUID HETERIC-BLOCK POLYOXYALKYLENE COMPOUNDS HAVING IMPROVED FLOWABILITY CHARACTERISTICS

[75] Inventors: Anthony G. Schaefer, Wyandotte; Sridhar Gopalkrishnan, Grosse Ile; Jay G. Otten, Flat Rock, all of Mich.; Richard J. Holland, Flanders, N.J.

[73] Assignee: BASF Corporation, Mount Olive, N.J.

[21] Appl. No.: 775,235

[22] Filed: Dec. 30, 1996

[51] Int. Cl.$^6$ .............................. A61K 7/16; A61K 7/18; A61K 7/20
[52] U.S. Cl. ................................. 424/52; 424/49; 424/53
[58] Field of Search ........................................... 424/49–58

[56] References Cited

U.S. PATENT DOCUMENTS

| | | |
|---|---|---|
| 3,639,574 | 2/1972 | Schmolka I . |
| 3,740,421 | 6/1973 | Schmolka II . |
| 3,867,533 | 2/1975 | Schmolka III . |
| 4,272,394 | 6/1981 | Kaneko . |
| 4,411,810 | 10/1983 | Dutton et al. . |
| 4,465,663 | 8/1984 | Schmolka IV . |
| 4,476,107 | 10/1984 | Schmolka V . |
| 4,925,988 | 5/1990 | Licht et al. . |
| 5,035,880 | 7/1991 | Mori et al. . |
| 5,057,307 | 10/1991 | Hill et al. . |
| 5,073,368 | 12/1991 | Subramanian . |
| 5,096,698 | 3/1992 | Mitchell et al. . |
| 5,187,191 | 2/1993 | Otten et al. . |
| 5,256,396 | 10/1993 | Piechota, Jr. . |
| 5,374,368 | 12/1994 | Hauschild I . |
| 5,424,060 | 6/1995 | Hauschild II . |
| 5,496,542 | 3/1996 | Hauschild III . |

FOREIGN PATENT DOCUMENTS

| | | |
|---|---|---|
| 546-627 | 6/1991 | United Kingdom . |
| WO 93/13750 | 7/1993 | WIPO . |

OTHER PUBLICATIONS

BASF Performance Chemicals Product Brochure; BASF Corporation; May 1997; Mount Olive, New Jersey.

*Primary Examiner*—Shep K. Rose
*Attorney, Agent, or Firm*—Joanne P. Will

[57] ABSTRACT

The present invention relates to liquid polyoxyalkylene compounds having improved flowability characteristics useful in a variety of industrial and personal care applications.

2 Claims, No Drawings

LIQUID HETERIC-BLOCK POLYOXYALKYLENE COMPOUNDS HAVING IMPROVED FLOWABILITY CHARACTERISTICS

FIELD OF THE INVENTION

The present invention relates to liquid heteric-block polyoxyalkylene compounds which are homogeneous and have improved flowability characteristics.

BACKGROUND

Polyoxyalkylene block copolymers are well known to those skilled in the non-ionic surfactant art. Specifically, U.S. Pat. No. 3,740,421 (Schmolka) assigned to BASF discloses aqueous gels prepared using a block copolymer of polyoxyethylene/polyoxypropylene suitable for pharmaceutical and personal care compositions. U.S. Pat. No. 3,639,574 (Schmolka) assigned to BASF discloses polyoxyethylene/polyoxypropylene block copolymers as gelling agents for hydrogen peroxide compositions. U.S. Pat. No. 4,465,663 (Schmolka) assigned to BASF discloses polyoxybutylene/polyoxyethylene block copolymers as gelling agents for aqueous gels useful in personal care and pharmaceutical applications. Some of these compounds are sold by the BASF Corporation under the PLURONIC® tradename.

Additionally, U.S. Pat. No. 4,272,394 and U.S. Pat. No. 4,411,810 disclose the use of polyoxyalkylene block copolymers in machine dishwashing applications. U.S. Pat. No. 4,925,988 discloses a nonionic surfactant employing a specific combination of alkanol, ethylene oxide and propylene oxide useful in an automatic dishwashing application. U.S. Pat. No. 5,374,368 describes the use of liquid EO/PO/EO triblock co-polymers (PLURONIC® L 31 and L 35 surfactants) in stable hydrogen peroxide releasing dental care compositions at levels of 55–90% by weight of the dental care composition. U.S. Pat. No. 3,740,421 discloses gel forming solid EO/PO/EO triblock copolymers useful in cosmetic and personal care formulations at levels of approximately 20–25% by weight. Preferred solid EO/PO/EO triblock copolymers have a molecular weight of 4,600–16,000. Said solid EO/PO/EO triblock copolymers form a gel when added to an aqueous solution. U.S. Pat. No. 3,867,533 discloses aqueous gel compositions containing solid EO/PO/EO triblock copolymers, having a molecular weight of 6,450–20,000 useful at levels of approximately 20% by weight. Said compositions are useful in preparing cosmetic formulations. U.S. Pat. No. 4,465,663 discloses clear aqueous cosmetic gels containing solid EO/BO (butylene oxide)/EO triblock copolymers at levels of approximately 20%. U.S. Pat. No. 5,035,880 discloses a stable dentifrice compositions containing a cetylpyridinium bactericide and EO/PO/EO solid triblock copolymers (PLURONIC® F 127 surfactant), and polyethylene glycol at levels of 15–80% by weight. U.S. Pat. No. 4,476,107 discloses a mouthwash containing EO/BO(butylene oxide)/EO triblock copolymers at levels of 0.5–5.0% by weight. U.S. Pat. No. 5,057,307 discloses oral hygiene gels containing non-ionic surfactants, coating substances; and viscosifiers. Said non-ionic surfactants are PLURONIC® F 108 and F 127 surfactants available from BASF Corporation, Mt. Olive, N.J. U.S. Pat. No. 5,256,396 discloses a topical composition comprising an EO/PO/EO solid triblock copolymer (PLURONIC® F 127 surfactant) used at a level of more than 10% to about 17% by weight. EPO-546-627A discloses mouthwash compositions comprising solid EO/PO/EO triblock copolymers such as PLURONIC® F 108, F88 surfactants at levels of 0.5–3% by weight. U.S. Pat. No. 5,073,368 discloses mouthwashes containing solid EO/PO/EO triblock copolymers such as PLURONIC® F 87 surfactant at levels of 0.1–3% by weight. WO 93/13750 discloses an ocular cleansing composition comprising solid PLURONIC® F 87 and paste PLURONIC® P 85 EO/PO/EO triblock copolymers. PLURONIC® P 85 surfactant is 4–9% by weight of the cleansing composition, PLURONIC® F 87 surfactant is 0.5–2% by weight of the cleansing composition. Finally, U.S. Pat. No. 5,096,698 discloses a dental creme composition containing a non-ionic triblock liquid EO/PO/EO copolymer or a solid triblock EO/PO/EO copolymer at levels of 0.1–5% by weight. Said copolymers help to prevent phase separation. PLURONIC® F 108 surfactant (solid) is most preferred, followed by PLURONIC (® F 87, PLURONIC® ) F 127, and PLURONIC® ) L 72 surfactants. U.S. Pat. No. 4,272,394 discloses novel, low foaming nonionic surfactant for machine dishwashing compositions. U.S. Pat. No. 4, 411,810 discloses a low foaming, low cloud point, nonionic surfactant for machine dishwashing compositions. U.S. Pat. No. 5,496, 542, U.S. Pat. No. 5,374,368, and U.S. Pat. No. 5,424,060 disclose the use of polyoxyalkylene compound for formulating a stable percarbonate formulation as well as a dentifrice composition. U.S. Pat. No. 5,187,191 discloses polyoxyalkylene heteric block surfactants in agricultural formulations. Finally, JP 47-48366 B4 discloses a process for producing tasteless, liquid, heteric polyoxyalkylene compounds of molecular weight 1000 or higher. However, a major problem with these polymeric materials is that they have high pour points (more close to ambient temperatures) which limits their use in processing cosmetic and toiletry compositions. Furthermore, the polymers of the JP 47-48366, B4 application develop a greater degree of crystallinity which manifest itself as haze and precipitated solids upon storage.

Applicants have surprisingly discovered a method for producing liquid, heteric-block polyoxyalkylene compounds with significantly lower pour points (i.e. more close to freezing temperatures) which substantially increases their utility in personal care compositions. Furthermore, the polymers of the Applicant's invention when neutralized with common inorganic acids result in compositions that are essentially clear and virtually free from precipitated solids during storage. Applicants have achieved this by selectively controlling the distribution or placement of propylene oxide and ethylene oxide in the polymers of the Applicant's invention. Without being limited by theory, the Applicants wish to stress that it is particularly important to control the distribution or placement of $C_3$ or higher alkylene oxides in the polymer chain, in order to effectively minimize or eliminate the formation of crystalline segments in the polymer. When the formation of crystalline segments in the polymer is allowed to occur, said crystalline segments fall out of solution resulting in a undesirable two-phase product. The Applicant's approach to overcome this problem in the art differs from the method disclosed in the JP 47-48366 B4 application wherein the alkylene oxides are randomly distributed throughout the polymer chain. Such polymers as disclosed in JP 47-48366 B4 comprised solely of a random distribution of alkylene oxides throughout the polymer chain are outside the scope of the Applicant's invention.

DEFINITIONS AND TERMS

HOMOGENEITY is a term used to characterize the single phase, physical form of the liquid, heteric-block polyoxyalkylene compound of this invention.

FLOWABILITY refers to the ease of pourability of the liquid polyoxyalkylene compounds of this invention. The ease of pourability is reflected in the pour points values shown for the liquid, heteric-block compounds.

HETERIC—BLOCK—The liquid polyoxyalkylene polymer of the present invention is a block copolymer of which at least one block is comprised of a mixture of ethylene oxide and $C_{3-6}$ alkylene oxides arranged randomly. Said random arrangement of ethylene oxide and $C_{3-6}$ alkylene oxides is referred to as a heteric-block.

SUMMARY

The present invention relates to a liquid heteric-block polyoxyalkylene compound having improved flowability and homogeneity characteristics having the formula:

$$l\text{-}[(AO)_a\text{-}[(EO)_b(XO)_c]\text{-}(EO)_d\text{-}M]_x;$$

wherein l is a initiator or a mixture of initiators having at least one substituent selected from the group including but not limited to OH, NH2, or COOH;

AO is a 2–6 Carbon alkylene oxide or a mixture of 2–6 carbon alkylene oxides arranged randomly or in a block sequence;

EO is ethylene oxide;

XO is an alkylene oxide moiety having 3–6 carbon atoms;

M is hydrogen or alkali or an alkaline earth metal;

a is an integer from about 1–20;

b is an integer from about 5–1500;

c is an integer from about 2–700;

d is an integer from about 1–15;

x is an integer from about 1–8;

The present invention further relates to a method for making a liquid, heteric-block polyoxyalkylene compound having improved flowability characteristics having the formula:

$$l\text{-}[(AO)_a\text{-}[(EO)_b(XO)_c]\text{-}(EO)_d\text{-}M]_x;$$

wherein l is an initiator or a mixture of initiators having at least one substituent selected from the group including but not limited to OH, NH2, or COOH;

AO is a $C_{2-6}$ alkylene oxide or a mixture of $C_{2-6}$ alkylene oxides arranged randomly or in a block sequence EO is ethylene oxide and XO is an alkylene oxide moiety having 3–6 carbon atoms;

M is Hydrogen or an alkali or an alkaline earth metal;

a is an integer from about 1–20;

b is an integer from about 5–1500;

c is an integer from about 2–700;

d is an integer from about 1–15;

x is an integer from about 1–8;

comprising the steps of:

a. adding AO to an initiator and catalyst followed by, b. adding a mixture of EO and XO followed by, c. adding EO.

The molecular weight range is about 1,000–100,000.

DETAILED DESCRIPTION

The present invention relates to a liquid heteric-block polyoxyalkylene compound having improved flowability and homogeneity characteristics having the formula:

$$l\text{-}[(AO)_a\text{-}[(EO)_b(XO)_c]\text{-}(EO)_d\text{-}M]_x;$$

wherein l is a initiator or a mixture of initiators having at least one substituent selected from the group including but not limited to OH, NH2, or COOH;

AO is a 2–6 Carbon alkylene oxide or a mixture of 2–6 carbon alkylene oxides arranged randomly or in a block sequence;

EO is ethylene oxide;

XO is an alkylene oxide moiety having 3–6 carbon atoms;

M is hydrogen or an alkali or alkaline earth metal;

a is an integer from about 1–20;

b is an integer from about 5–1500;

c is an integer from about 2–700;

d is an integer from about 1–15;

x is an integer from about 1–8;

The present invention further relates to a method for making a liquid heteric-block polyoxyalkylene compound having improved flowability characteristics having the formula:

$$l\text{-}[(AO)_a\text{-}[(EO)_b(XO)_c]\text{-}(EO)_d\text{-}M]_x;$$

wherein l is a initiator or a mixture of initiators having at least one substituent selected from the group including but not limited to OH, NH2, or COOH;

AO is a $C_{2-6}$ alkylene oxide or a mixture of $C_{2-6}$ alkyleneoxides arranged randomly or in a block sequence;

EO is ethylene oxide and XO is an alkylene oxide moiety having 3–6 carbon atoms;

M is hydrogen or alkali or an alkaline earth metal;

a is an integer from about 1–20;

b is an integer from about 5–1500;

c is an integer from about 2–700;

d is an integer from about 1–15;

x is an integer from 1–8;

comprising the steps of:

a. adding AO to an initiator and catalyst followed by, b. adding a mixture of EO and XO followed by, c. adding EO.

Preferably, the initiator is selected from propylene glycol (PG), dipropylene glycol, ethylene glycol, diethylene glycol, and glycerol, most preferably the initiator is propylene glycol (PG). Said initiator has at least one substituent selected from the group including but not limited to OH, NH2, or COOH.

AO is an alkylene oxide moiety having 2–6 carbons, preferably, said alkylene oxide moiety is ethylene oxide, propylene oxide or butylene oxide, more preferably ethylene oxide, propylene oxide or ethylene oxide and propylene oxide, most preferably ethylene oxide or ethylene oxide and propylene oxide. Further, AO can be a mixture of 2–6 carbon alkylene oxides arranged randomly or in block sequences.

XO is an alkylene oxide moiety having 3–6 carbons, preferably said alkylene oxide moiety is propylene oxide or butylene oxide, most preferably propylene oxide.

M is H or a catalyst selected from the group including but not limited to alkali or alkaline earth metal bases, lithium hydroxide, calcium hydroxide, potassium hydroxide, cesium hydroxide, most preferably potassium hydroxide.

a is preferably about 1–20, more preferably about 1–10, most preferably about 2–8.

b is preferably about 5–1500, more preferably about 5–500, most preferably about 7–16.

c is preferably about 1–700, more preferably about 1–250, most preferably about 1–10.

d is preferably about 1–15, more preferably about 1–10, most preferably about 1–5.

x is preferably about 1–8, more preferably about 2–3, most preferably is 2.

The molecular weight range is about 1,000–100,000.

The more preferred values for molecular weight are from about 1,000–25,000.

The most preferred molecular weight is from about 1,000–3,000.

DESCRIPTION OF THE METHOD OF MAKING THE LIQUID HETERIC-BLOCK POLYOXYALKYLENE THE PRESENT INVENTION

Note: The ethylene oxide and mixed oxide charges in these experiments were added under a 34 psig nitrogen pad with addition rates to keep the vapor phase EO concentration below the safe explosive limit which can be calculated according to Siwek in Siwek, R., Rozenberg, E., "Ethylene Oxide Vapor Decomposition-Process and Protective Measures", Zeitschrift fur die Fett-, Ol-, Tensid-, Kosmetik- und Pharmaindustrie, 115, Augsburg, Sep. 1, 1989, NR14-1.

A two gallon stainless steel autoclave was charged with 1089 g of propylene glycol, 46.6 g of 45% potassium hydroxide and purged with nitrogen. The contents were heated to 80° C. and stripped to remove volatiles for 2.5 hours. The contents were heated to 130° C. and the pressure in the vessel adjusted to 34 psig with nitrogen.

Ethylene oxide (4412.9 g) was added over a period of six hours. After the addition was finished the mixture was kept at 130° C. for one hour and then volatiles stripped for ½ hour.

A five gallon stainless steel autoclave was charged with 3075.6 g of the above material and purged with nitrogen. The material was heated to 116° C. and 11,168 g of a mixture of 76.8 weight % Ethylene Oxide and 23.2 weight % Propylene Oxide added over a period of 9.5 hours. After the addition was complete, the mixture was kept at 116° C. for an additional two hours. A final charge of 1762 g of Ethylene Oxide was added over two hours and then kept at 116° C. for 2.5 hours. The mixture was stripped for ½ hour, cooled to 80° C. and 30.1 g of 50% Hypophosphorous acid or 17.5 g of 85% Phosphoric acid added. The mixture was agitated for ½ hour in the autoclave and then discharged.

As an alternative, the material may be treated with Magnesium Silicate and filtered rather than neutralized with acid.

Sample A is a comparison sample of an all heteric material similar to JP 4748366 B4

$$PG\text{-}[(EO_{18.2}\backslash PO_{2.8})H]_2$$

Sample B of the present invention has the structure:

$$PG[(EO)_{3.5}(EO_{12.2}\backslash PO_{2.8})(EO)_{2.5}H]_2$$

Sample C of the present invention has the structure:

$$PG[(EO)_6(PO)_1(EO_{8.2}\backslash PO_{1.8})(EO)_4H]_2$$

Sample D of the present invention has the structure:

$$PG[(EO)_{3.5}(EO_{11.5}\backslash PO_{3.3})(EO)_{2.5}H]_2$$

Sample E of the present invention has the structure:

$$PG[(EO)_6(PO)_{1.7}(EO_{7.5}\backslash PO_{1.7})(EO)_4H]_2$$

Sample F is a comparison sample of an all heteric material similar to JP 4748366 B4:

$$PG\text{-}[(EO_{17}\backslash PO_{3.7})H]_2$$

Sample G of the present invention has the structure:

$$PG[(EO)_{3.5}(EO_{11}\backslash PO_{3.7})(EO)_{2.5}H]_2$$

Sample H of the present invention has the structure:

$$PG[(EO)_6(PO)_{1.9}(EO_7\backslash PO_{1.9})(EO)_4H]_2$$

Comparison of the 20% PO all heteric material A with 20% PO heteric-block materials made according to this invention (B and C) shows that A exhibits a considerably higher pour point. The 25% PO materials, F, G and H exhibit similar behavior. Examples D and E are given as further evidence of the trend of lower pour points when materials are made according to this invention.

The amount of settled material in these samples is also considerably less for those made incorporating heteric-blocks according to this invention.

TABLE 1

Comparison of the Present Invention with Polyethylene Glycol 400 and Heteric Materials

| Material | PEG | PEG | A | B | C | D | E | F | G | H |
|---|---|---|---|---|---|---|---|---|---|---|
| | 400 | 2000 | 20% PO | 20% PO | 20% PO | 23% PO | 23% PO | 25% PO | 25% PO | 25% PO |
| Mol Wt | 400 | 2000 | 2000 | 2000 | 2000 | 2000 | 2000 | 2000 | 2000 | 2000 |
| Pour Point °C. | 5.0 | 52.0 | 13 | 9 | 4.4 | 3.3 | −0.5 | 6.1 | −3.9 | −5.0 |
| Amount of settle*(@21° C.) | none | solid | ++++ | +++ | +++ | ++ | ++ | ++ | <+ | + |
| Taste | very bitter | very mild taste | very mild taste | very mild taste | very mild taste | very mild taste | very mild taste | very mild taste | very mild taste | very mild taste |

*++++ most settling
+ least settling, slight solid present.

PEG 400 is a 400 Molecular weight polyethylene glycol.

PEG 2000 is a 2000 Molecular weight polyethylene glycol.

The percent Propylene Oxide (PO) is calculated as the total weight percent contributed by the propylene glycol (PG) initiator and propylene oxide.

Comparison of the pour point of Polyethylene Glycol 400 with Examples C, D, E, G and H of the present invention shows a lowering of the pour point despite the fact that the molecular weights of these materials are much higher. The pour point for a PEG 2000 is 52° C.

Utility of the Polyoxyalkylene Compounds Having Improved Flowability

Because the polyoxyalkylene compounds made according to the method described hereinabove have improved flowability characteristics, they are useful in a variety of personal care and pharmaceutical applications, particularly as carriers for personal care compositions.

Personal Care

The compounds prepared according to the method of the present invention are particularly useful in personal care compositions, in particular oral care compositions, such as toothpaste. Dentifrice formulations typically contain substantial amounts of humectants. Humectants help the formulation retain its moisture, thus preventing the formulation from hardening, when the container cap is left open for extended periods. Typical humectants employed in such formulations are glycerol, sorbitol which are usually the preferred humectants because of their sweet taste. Other humectants which are also used are polyethylene glycols of molecular weight typically between 200–600. For economic reasons, a combination of humectants is used in the majority of personal care formulations. More recently, toothpaste compositions are being formulated without any significant incorporation of water. Examples of such toothpaste compositions are those that cannot tolerate the presence of significant levels of water due to concerns related to decomposition of key ingredients leading to loss of activity, or reactivity of ingredients, for example, baking soda and a peroxygen compound, such as, hydrogen peroxide or sodium percarbonate. The formulation and increased stability of such toothpaste compositions is achieved by employing a non-aqueous carrier typically selected from low molecular weight liquid polyethylene glycols. Dentifrice compositions comprising a peroxygen source and baking soda are typically formulated by pre-blending dentifrice ingredients in the presence of a liquid carrier, such as a liquid polyethylene glycol to achieve a composition with toothpaste like consistency. The choice of liquid polyethylene glycols as carriers for non-aqueous formulations comes with several advantages, such as good hygroscopicity, low viscosity, good compatibility with several ingredients, low volatility, low cost, low toxicity, low odor, and low pour point. However, a significant drawback associated with the use of low molecular polyethylene glycol is its bitter taste. The bitter taste of the liquid polyethylene glycols lends an unpleasant taste to the finished formulation which has to be often masked by the inclusion of expensive sweeteners or masking agents. Many pharmaceutical compositions which are administered orally, and further limited to the use of liquid polyethylene glycols as carriers currently have little flexibility in altering the bitter taste of the resulting composition. The liquid, heteric-block polyoxyalkylene glycols of the present invention, which are essentially clear, virtually free from precipitates, and do not have a bitter taste, can serve as a suitable carrier for various personal care, oral care and pharmaceutical compositions that come in contact with the human body.

Preparation of Personal Care Compositions Containing The Novel Polyoxyalkylene Compound of the present Invention The liquid, heteric-block polyoxyalkylene compounds of the present invention are present in personal care compositions at a preferred level of 1–99%, more preferably at a level of 20–79%; most preferably at a level of 30–50% by weight of the personal care composition. Generally, the level of incorporation depends on the end use of the liquid polyoxyalkylene compound of the invention. If they function as carriers, for example, in a essentially non-aqueous dentifrice formulation, then higher use levels are required in the formulation.

Personal care formulations may also contain other ingredients such as surfactants selected from anionic surfactants which include sodium lauryl sulphate; sodium alkyl glyceryl ether sulfonate; alkyl benzene sulfonates. Other anionic surfactants also include oxyalkylates of $C_6$–$C_{18}$ alcohols. It is also known to those skilled in the art to use solid block copolymers of polyoxyethylene and polyoxypropylene to further provide a boost in the foaming performance of the dentifrice composition. Further, small amounts of cationic surfactants, having a quaternary nitrogen, which show compatibility with the nonionic carrier blends of this invention can also be used. Various other materials may also be used in the formulating of personal care products. For example, peroxygen compounds such as hydrogen peroxide, sodium percarbonate, can be used in such dentifrice compositions. in a dentifrice, dental abrasives consisting of finely divided silica, or calcium carbonate, sodium bicarbonate, calcium pyrophosphate, and hydrated alumina are added for polishing performance. Additionally, thickening agents such as xanthan gum, gum arabic, hydroxyethylcellulose, polyvinylpyrrolidone, gum tragacanth, carragennan can also be used to provide sufficient thickening consistency to the formulation. Also, flavoring agents such as peppermint, spearmint oils or preservatives, opacifying agents, buffer salts, sweeteners, anti-bacterial agents or anti-plaque agents, anti-inflammatory agents, anti-caries agents such as the fluoride salts can also be included in small amounts. Polymeric agents which accelerate the transport of active materials can also be included. Also, in cosmetic creams emollients such as glycerin, mineral oil and petrolatum can be added.

Personal care products are formulated according to methods known to those skilled in the art. Representative personal care product formulations are disclosed in: *Cosmetics, Science and Technology,* 2nd Edition, Vol. 1, Edited by M. S. Balsam, et al., and *A Formulary of Cosmetic Preparations,* Michael and Irene Ash, Chemical Publishing, N.Y., N.Y., both incorporated by reference herein.

The following non-limiting Examples will further serve to illustrate the utility of the present invention. All percentages are weight percent (%) of the total composition unless otherwise indicated.

Dentifrice Composition 1 to 55% abrasive, selected from the group including, but riot limited to, anhydrous dicalcium phosphate, calcium carbonate, calcium pyrophosphate and sodium bicarbonate.

0 to 0.6% of a fluoridating agent, including, but not limited to stannous fluoride, sodium fluoride, sodium monofluorophosphate.

2 to 10% binders, including, but not limited to, gum karaya, tragacanth USP, sodium alginate; Irish moss and methyl cellulose.

0 to 10% of a peroxygen source, including but not limited to hydrogen peroxide, sodium percarbonate.

0 to 8% surfactants, including, but not limited to, sodium lauryl sulfate, sodium-N-lauryl sarcosinate; dioctyl sodium sulfosuccinate.

0 to 5% block copolymers of EO and PO.

5 to 50% humectants, including, but not limited to, glycerin; propylene glycol; sorbitol; polyethylene glycol.

5 to 70% polyoxyalkylene compound having the formula:

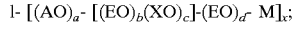

wherein l is a initiator or a mixture of initiators having at least one substituent selected from the group including but not limited to OH, NH2, or COOH;

AO is a 2–6 carbon alkylene oxide or a mixture of 2–6 carbon alkylene oxides arranged randomly or in a block sequence;
EO is ethylene oxide;
XO is an alkylene oxide moiety having 3–6 carbon atoms;
M is hydrogen or an alkali or alkaline earth metal;
a is an integer from about 1–20;
b is an integer from about 5–1500;
c is an integer from about 2–700;
d is an integer from about 1–15;
x is an integer from about 1–8;

Body Wash Composition 1 to 5% emollients, including, but not limited to, lanolin, sterols (cholesterol) and fatty acids.

0.1 to 3% barrier agents, including but not limited to, petrolatum, beeswax; casein.

0.01 to 0.1% healing agents, including, but not limited to, allantoin and urea.

2 to 20% humectants, including, but not limited to, glycerin; propyleneglycol; sorbitol; polyethylene glycol.

0.01 to 1% thickeners, including but not limited to, guar gum, cellulose derivatives and Irish moss.

0.5 to 3% emulsifiers, including, but not limited to, cetyl pyridimium chloride; polyoxyethylene lauryl alcohol 5 to 70% polyoxyalkylene compound having the formula:

$$l\text{-}[(AO)_{a\text{-}[(EO)_b}(XO)_c]\text{-}(EO)_d\text{-}M]_x;$$

wherein l is a initiator or a mixture of initiators having at least one substituent selected from the group consisting of OH, NH2, or COOH;

AO is a 2–6 Carbon alkylene oxide or a mixture of 2–6 carbon alkylene oxides arranged randomly or in a block sequence;
EO is ethylene oxide;
XO is an alkylene oxide moiety having 3–6 carbon atoms;
M is hydrogen or an alkali or alkaline earth metal;
a is an integer from about 1–20;
b is an integer from about 5–1500;
c is an integer from about 2–700;
d is an integer from about 1–15;
x is an integer from about 1–8;

Antiperspirant Deodorant Composition 36 to 50% aluminum chlorhydrate or
1 to 15% zinc oxide or
1 to 15% boric acid
5 to 70% polyoxyalkylene compound:

$$l\text{-}[(AO)_a\text{-}[(EO)_b(XO)_c]\text{-}(EO)_d\text{-}M]_x;$$

wherein
is a initiator or a mixture of initiators having at least one substituent selected from the group including but not limited to OH, NH2, or COOH;
AO is a 2–6 Carbon alkylene oxide or a mixture of 2–6 carbon alkylene oxides arranged randomly or in a block sequence;
EO is ethylene oxide;
XO is an alkylene oxide moiety having 3–6 carbon atoms;
M is hydrogen or an alkali or alkaline earth metal;
a is an integer from about 1–20;
b is an integer from about 5–1500;
c is an integer from about 2–700;
d is an integer from about 1–15;
x is an integer from about 1–8;
25 to 50% SD alcohol (40)

Antiperspirant compositions may also contain emollients and perfume.

What is claimed is:

1. A dentifrice composition comprising:

1 to 55% abrasive, selected from anhydrous dicalcium phosphate, calcium carbonate, calcium pyrophosphate and sodium bicarbonate, an effective amount up to 0.6% of a fluoridating agent selected from stannous fluoride, sodium fluoride, sodium monofluorophosphate;

2 to 10% binders selected from gum karaya, tragacanth USP, sodium alginate; Irish moss and methyl cellulose;

an effective amount up to 10% of a peroxygen source selected from hydrogen peroxide, sodium percarbonate;

an effective amount up to 8% of surfactants selected from sodium lauryl sulfate, sodium-N-lauryl sarcosinate; dioctyl sodium sulfosuccinate;

an effective amount up to 5% of a solid triblock copolymer of EO and PO;

an effective amount up to 50% of humectants selected from glycerin; propylene glycol; sorbitol; polyethylene glycol;

5 to 70% of a liquid polyoxyalkylene having the formula:

$$l\text{-}[(AO)_a\text{-}[(EO)_b(XO)_c]\text{-}(EO)_d\text{-}M]_x;\text{ wherein}$$

l is a initiator or a mixture of initiators having at least one substituent selected from the group including but not limited to OH, NH2, or COOH;
AO is ethylene oxide or ethylene oxide and propylene oxide;
XO is propylene oxide;
M is H or an alkali or alkaline earth metal;
a is an integer from about 1–10;
b is an integer from about 5–500;
c is an integer from about 1–250;
d is an integer from about 1–10;
x is an integer from 2–3.

2. The dentifrice composition of claim 1, wherein the initiator l is propylene glycol, AO is ethylene oxide or ethylene oxide and propylene oxide, XO is propylene oxide, M is H, a is 2–8, b is 7–16, c is 1–10, d is 1–5, and x is 2.

* * * * *